Figure 1:
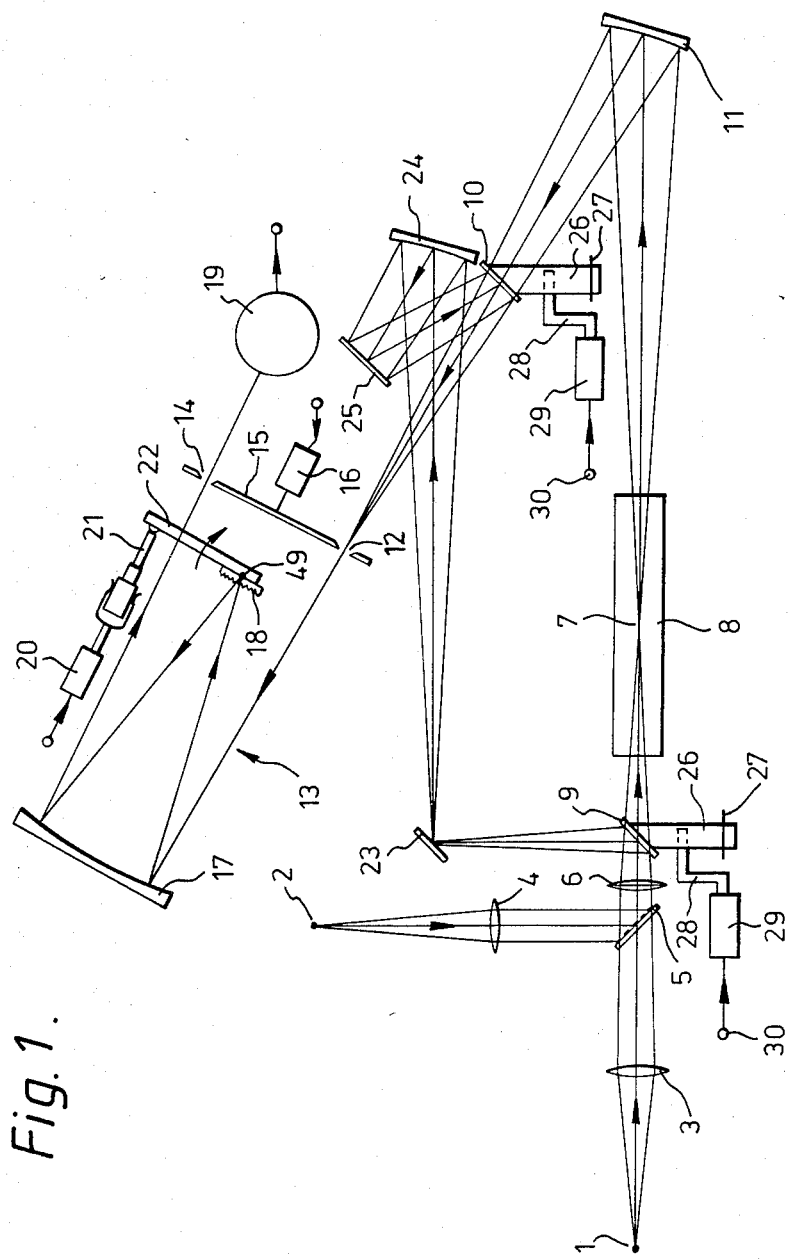

United States Patent [19]

Morley et al.

[11] Patent Number: 4,519,706

[45] Date of Patent: May 28, 1985

[54] SPECTROPHOTOMETER HAVING WAVELENGTH SELECTING STRUCTURE

[75] Inventors: Peter Morley, Newmarket; Peter J. Little, Malmesbury, both of England

[73] Assignee: U.S. Philips Corporation, New York, N.Y.

[21] Appl. No.: 458,123

[22] Filed: Jan. 14, 1983

[30] Foreign Application Priority Data

Jan. 19, 1982 [GB] United Kingdom ............... 8201372

[51] Int. Cl.³ ................. G01J 1/42; G01N 21/71
[52] U.S. Cl. .................................. 356/319; 356/325
[58] Field of Search ........ 356/311, 315, 319, 323–325, 356/332, 334; 364/497, 498

[56] References Cited

U.S. PATENT DOCUMENTS 4,171,913 10/1979 Wildy et al. ..................... 356/325
4,227,811 10/1980 Tohyama et al. ................ 356/319

FOREIGN PATENT DOCUMENTS 1397286 6/1975 United Kingdom ............... 356/334

OTHER PUBLICATIONS

Spillman et al., *Analytical Chemistry*, vol. 48, No. 2, Feb. 1976, pp. 303–311.
Floyd et al., *Analytical Chemistry*, vol. 52, No. 3, Mar. 1980, pp. 431–438.

*Primary Examiner*—F. L. Evans
*Attorney, Agent, or Firm*—Paul R. Miller

[57] ABSTRACT

In atomic spectrophotometers comprising a source of radiation characteristic of an element to be detected in a sample, a monochromator for selecting a desired spectral line from radiation received from the source by the sample, and a detector for producing an output signal from the monochromator output radiation, the monochromator is accurately tuned to the desired line to obtain a maximum detector signal, and simultaneously, the gain of the detector is adjusted to keep the signal magnitude within the best working range of subsequent signal processing circuits. In accordance with the present invention, both adjustments are made simultaneously by comparing an amplified detector signal with a desired reference signal level corresponding to the best signal magnitude, and using the difference between them to adjust the gain of the amplified detector signal in a closed loop control system to continuously equalize the amplified detector signal with the reference level. The monochromator is tuned, preferably by an automatic device, to seek a minimum value of amplifier gain, at which the detector output will be a maximum at the peak of the spectral line with the amplified detector output being simultaneously equal to the desired reference level. The amplifier gain is then set to the values so obtained by a digital-analog converter, and absorption measurements are made with the control loop open.

12 Claims, 2 Drawing Figures

SPECTROPHOTOMETER HAVING WAVELENGTH SELECTING STRUCTURE

The invention relates to a spectrophotometer comprising a source of radiation, a monochromator arranged to receive radiation from the source, a detector for receiving a selected wavelength of radiation from the monochromator and producing a signal representative of the intensity of the radiation received, means for comparing the output of the detector with a reference value when the spectrophotometer is in a calibration mode and producing a control signal dependent on the comparison, means for feeding the control signal to a control input of the detector for controlling the gain thereof so as to cause its output to tend towards the reference value, means for storing the control signal, and means for applying the stored control signal to the control input of the detector when the spectrophotometer is in a measurement mode.

Such a spectrophotometer is disclosed in U.K. patent application No. 2075188A.

The magnitude of the detector signal may vary widely with instrumental conditions such as the pass band of the monochromator. Adjustable amplification should be provided for the detector signal so that the maximum signal obtained with a given sample can be set to be a large fraction of the maximum signal that can be handled by subsequent measurement circuits, ensuring that as wide a range of signal amplitudes as possible can be measured.

In an atomic spectrophotometer resonance line radiation emitted by the source, which may be the atomised sample is relatively narrow in spectral width. In consequence, a factor which strongly influences the amount of radiation reaching the detector is the wavelength setting of the monochromator. It is important to ensure that the monochromator is set to the peak wavelength of the selected resonance line to ensure the best signal to noise ratio at the detector. As the monochromator is brought into tune the amount of radiation received by the detector varies widely until the peak is reached.

U.K. patent specification No. 1397286 discloses an atomic spectrophotometer including a monochromator, a detector responsive to the radiation beam from an exit slit of the monochromator to generate an electric output, and an arrangement capable of automatically fine tuning the monochromator wavelength when a selected spectral line has been positioned at least partly within the exit slit; in which the arrangement includes an electromechanical transducer adapted to adjust the monochromator wavelength, a d.c. amplifier adapted to bias the transducer, an electrical oscillator adapted to cyclically drive the transducer at a predetermined frequency so as to vibrate an element in the monochromator and thereby produce a signal component at the frequency in the output of the detector, and means responsive to the signal component to produce a change of level at the input of the d.c. amplifier, and in which the transducer, monochromator, detector, input level changing means and d.c. amplifier function in a closed loop servo system which reduces the amplitude of the signal component at the frequency and adjusts the bias on the transducer to a value at which the selected spectral line is centered by the element on the monochromator exit slit.

It is an object of the invention to provide an alternative means of setting the wavelength passed by a monochromator in an atomic spectrophotometer.

The invention provides a spectrophotometer as described in the opening paragraph characterised in that the spectrophotometer is an atomic spectrophotometer and includes a source of resonance line radiation, means for stepping the selected wavelength of the monochromator through the resonance line when the spectrophotometer is in the calibration mode, means for detecting the magnitude of the control signal when the gain of the detector is at a minimum value, means for detecting the wavelength setting of the monochromator when the gain of the detector is at a minimum value, means for storing the magnitude of the control signal and the wavelength setting which give the minimum detector gain, and means for applying the stored control signal to the detector and the stored wavelength setting to the monochromator when the spectrophotometer is in the measurement mode.

The invention enables the realisation of a spectrophotometer in which the setting of the wavelength of the monochromator can be carried out simultaneously with the setting of the detector gain using components common to both processes. This enables a simpler and less expensive construction while allowing adjustment to obtain the best signal to noise ratio by adjustment of the detector gain.

The spectrophotometer may be characterised in that radiation from the source is passed through and is partly absorbed by the atomised sample and in that the stored control signal and stored wavelength setting are those obtained when a blank sample is atomised.

Alternatively the spectrophotometer may be an atomic emission spectrophotometer characterised in that the stored control signal and stored wavelength setting are those obtained when a sample containing a maximum concentration of the element is atomised.

In an atomic absorption spectrophotometer a sample to be analysed may be atomised in a flame to which it is carried in solution in nebulised droplets. The flame and the solvent free from the sample, referred to as a blank sample, will produce some absorption of the radiation. This absorption can be compensated for if the stored control signal, and hence the amplifier gain, is that obtained when a blank sample is atomised.

An atomic spectrophotometer according to the invention may be further characterised in that a sample path in which the sample is atomised is provided for the radiation between the source and the monochromator, in that an alternative reference path which excludes the sample is provided for the radiation between the source and the monochromator, and in that means are provided for deriving the stored wavelength setting and the stored control signal while the radiation is diverted via the reference path.

This gives the advantage that the setting of the monochromator is effected using radiation which has not passed through the flame. The flame introduces noise like fluctuations into the intensity of radiation received by the detector which makes it more difficult to locate the peak accurately.

An atomic absorption spectrophotometer according to the invention may be still further characterised in that the radiation passes to the detector via the sample path during sample measurements and via the reference path between sample measurements in the calibration mode.

In some spectrophotometers such a reference path is provided with beam chopping means which rapidly and continuously alternates the radiation between the reference path and the sample path while measurements are in progress. The detector signals for the two paths are separated by electronic switching means driven in synchronism with the beam chopping means and used to provide compensation for instrumental drift due mainly to source brightness drift and to detector sensitivity drift. The average radiation available for sample measurements is thereby reduced, regarding the signal to noise ratio of the detected signal. In a spectrophotometer according to the present invention the means for providing the reference path may be such that the radiation passes to the detector via the sample path during sample measurements and via the reference path between sample measurements when reference measurements are made. The invention can, however, also be applied equally well to chopped beam spectrophotometers.

An atomic spectrophotometer in accordance with the invention may be characterised in that the sample measurements and the calibration are carried out automatically under the control of a microprocessor with the stored control signal and stored wavelength setting obtained in the calibration mode being digitized and stored in the microprocessor memory for use during sample measurements.

An atomic spectrophotometer in accordance with the invention may be further characterised in that the reference value is a d.c. voltage and in that the amplified difference between this voltage and the detector signal comprises the control signal.

An atomic spectrophotometer in accordance with the invention may be yet further characterised in that the detector comprises a photomultiplier tube, and in that the control input is connected to means for varying the dynode potentials of the electron multiplier section of the photomultiplier tube to vary the detector gain.

Figure 2:
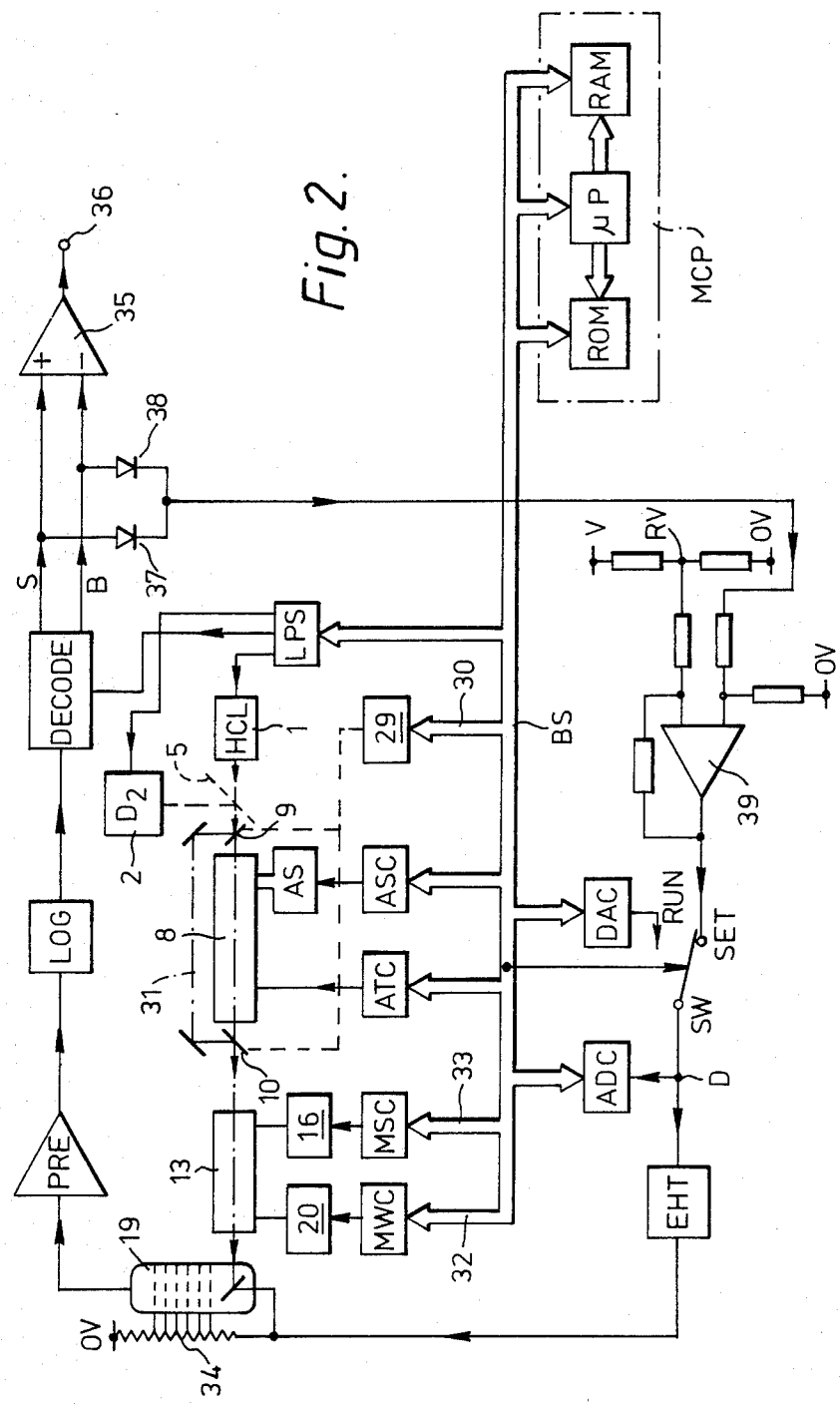

An embodiment of the invention will now be described, by way of example, with reference to the accompanying drawings, in which:

FIG. 1 shows the optical and mechanical layout of an atomic absorption spectrophotometer to which the invention can be applied, and FIG. 2 shows a system block diagram of control means suitable for applying the invention to the spectrophotometer of FIG. 1.

Referring to FIG. 1, a source 1 provides resonance line radiation characteristic of an atomic element to be detected and measured. Source 1 may be a hollow cathode lamp (HCL), or an electrodeless discharge lamp (EDL), each containing a sample of the element. A background source 2 provides radiation which is substantially constant as a function of wavelength over the pass band to be used. Typically, source 2 is a deuterium filled hollow cathode lamp.

Two lenses 3 and 4 provide approximately collimated beams, from the sources, impinging upon a "speckled" beam combining mirror 5. This mirror comprises a transparent substrate onto which a metal mirror has been evaporated via a mask having an array of apertures such that the total aperture area equals the remaining mask area. Thus, the intensities of both beams are halved and the beams are superposed. A further lens 6 images both sources onto the center 7 of a flame above a burner 8, which flame rises normal to the plane of the drawing.

The sample path with first be described and for this purpose, two moveable mirrors 9 and 10 are presumed to have been moved out of the radiation paths by mechanisms to be described later. The flame center 7 is imaged by an off-axis spherical mirror 11 at unity magnification onto the entrance slit 12 of a monochromator 13. Up to slit 12 the beams are shown as cones of rays but within the monochromator only the chief ray of the beam is shown for clarity. The entrance slit 12 and the exit slit 14 are mounted upon a disc 15 which may be rotated by a motor 16 to bring any one pair of a number of pairs of diametrically opposite slits, covering a range of slit widths, into operation. The monochromator 13 is of Ebert design in which the slit plate is in the focal plane of a spherical mirror 17. Thus, the beam is collimated by mirror 17 and reflected onto a reflective diffraction grating 18 where it is dispersed and reflected back to mirror 17. The beam is then refocussed onto the exit slit 14 through which it passes to a detector 19 which is a side-window photomultiplier tube shown end-on. The grating lines are normal to the plane of the drawing. The grating is rotatable about an axis 49 normal to the drawing and is driven by a stepping motor 20, via a micrometer 21 and a sine bar 22, to bring light of the desired wavelength onto the exit-slit.

The reference path is obtained when the mirrors 9 and 10 are in the position shown in FIG. 1. The coincident and convergent beams are then brought to a focus at a fixed mirror 23 which is comparatively small in area since the beam diameter is small at this point. The point of reflection at mirror 23 then corresponds to the flame center 7. The mirror 23 is set to reflect the chief ray of the beam parallel to the chief ray through the flame. An off-axis spherical mirror 24 of the same focal length as mirror 11 is placed at the same distance from mirror 23 as point 7 is from mirror 11 and at the same orientation as mirror 11. Thus, the magnification and the off-axis aberrations caused by the two spherical mirrors are the same. A fixed mirror 25 and moveable mirror 10 then bring the beam back onto the sample path so that it is again focussed on the entrance slit 12.

It is a virtue of this optical layout that, when the sample path is in use, there is only one optical component, spherical mirror 11, between the flame and the monochromator entrance slit, thus minimising the sample beam intensity reduction by absorption at mirror surfaces. The presence of four additional mirror surfaces in the reference path is not a disadvantage since flame noise is absent and the gain following the photomultiplier can be increased to provide an adequate reference signal while still maintaining optimum sample energy.

In FIG. 1 the movable mirrors 9 and 10 are shown schematically mounted upon an arm 26 pivoted about an axis 27 parallel to the plane of the drawing. A crank 28 driven by a motor 29 is shown schematically lifting arm 26 and mirror 9 or 10 out of the beam in response to an input command 30.

Referring to FIG. 2, the system block diagram, components corresponding to those in FIG. 1 are similarly numbered. The line source 1 and the background source 2 are fed with pulses of current from the lamp power supply LPS. The pulses to line source 1 alternate with the pulses to background source 2. Timing pulses are fed by LPS to a signal decoder DECODE to enable the signal pulses resulting from the radiation pulses to be separated into a sample channel and a background channel. The reference path 31 excluding the atomising burner 8 is shown schematically as are the moveable mirrors 9 and 10 driven by motors 29 in response to input 30 of FIG. 1. Samples to be analysed by the spectrophotometer are fed into the atomiser 8, operated by an atomiser control means ATC, from an automatic sampler AS operated by an automatic sampler control means ASC. The wavelength of the radiation passed by the monochromator 13 is selected by a wavelength control means MWC which receives a wavelength signal 32 and feeds motor 20 in FIG. 1. The bandpass, that is to say the slit width of monochromator 13, is selected by a slit control means MSC which receives a slit signal 33 and feeds motor 16 in FIG. 1.

A dynode voltage supply chain 34 for the photomultiplier detector 19 is fed from a variable voltage d.c. power supply EHT. The voltage output of EHT is set by a control signal D. Since the gain of photomultiplier 19 is a strong function of dynode supply chain voltage, the power supply EHT and detector 19 together constitute a controlled gain amplifier for the detector signal under the control of signal D. A pre-amplifier PRE converts the current output of photomultiplier 19 into a low output impedance voltage source suitable for feeding a unit (LOG) which provides a voltage output proportional to the logarithm of its input. In addition to separating the LOG output pulses into two separate channels, a DECODE unit also converts these pulses into two d.c. signals S and B, by means of sample-and-hold circuits, for the sample and background channels respectively. Subtraction of the B signal from the S signal in a subtractor 35 provides an absorbance signal at an output 36. Two diodes 37 and 38 pass the larger of signals S and B to one input of a differential amplifier 39, the other input of which is fed with a preselected reference voltage RV which is a large fraction of the maximum signal voltage S or B.

The amplified difference between RV and the larger of the S and B signals is fed to the SET contact of a changeover switch SW. With the pole of the switch in the SET position, the difference signal supplies control signal D, thus completing closed servo loop control over the controlled gain amplifier. The amplifier gain is set so that the larger of the S and B signals equals RV to an accuracy which is governed by the total loop gain. The control signal D is fed to an analogue-to-digital converter ADC which converts signal D into digital form suitable for indefinite storage without degradation. When measurements are to be made on samples, the stored signal D can be applied to a digital to analogue converter DAC which supplies the control signal to the RUN contact of switch SW. With the switch in the RUN position closed loop control is removed and the EHT, and hence the amplifier gain, will be set to the optimum value established in the SET position.

When the loop is closed, variations in the amount of radiation received by detector 19 will not show up as corresponding variations in the signals S or B. These signals will remain substantially constant, apart from the small servo loop error signals superposed on them. The radiation variations show up as variations in the signal D. If the received radiation increases, for example, the control signal changes so as to reduce EHT and so reduce the photomultiplier gain, thus maintaining the S or B signals constant and equal to the preselected value RV in spite of the increase in received radiation.

Desirably, the stored control signal D is that obtained when a blank sample is atomised since then absorption by the element carrier and the flame will be compensated. To achieve this, the moveable mirrors 9 and 10 are lifted out of the beam so that the sample path through the flame is used. Automatic sample control ASC then controls the automatic sampler AS to select a blank sample for aspiration into the atomising flame. Once the flame has stabilised and the value of D has settled with SW in the SET position, the digitised value of D is stored. SW is then returned to the RUN position for subsequent samples containing the element to be atomised and measured.

The closed loop gain control system is also used to fine tune the monochromator 13 onto the selected resonance line of the element. As pointed out above, when the loop is closed (SW in SET position) variations of radiation received at the detector show up as variations in the control signal D. As the monochromator is tuned through the resonance line, the radiation received will increase to a maximum and then fall off. Simultaneously, in closed loop gain control, the amplifier gain will fall to a minimum and then rise again. The polarity of the changes in signal D is arbitrary being governed by the detailed design of the EHT unit. The polarity of amplifier 39 is chosen to give negative feedback. For convenience it will be assumed that D is a positive going d.c. signal and that the EHT increases with increasing D signal. In this case, D will fall to a minimum as the wavelength peak is reached. Thus if the monochromator 13 is driven through the selected line and a record kept of the variation of signal D with selected wavelength, the monochromator can subsequently be set to the selected wavelength associated with the minimum value of D recorded and stored.

The stepping motor 20, described in relation to the rotatable diffraction grating 18 shown in FIG. 1, is shown schematically in FIG. 2 and provides a motor driven means for adjusting the selected wavelength.

The sequence of events to set the monochromator to a chosen spectral line is as follows. First, the setting of the stepper motor is determined which corresponds to the grating zero order. In the zero order, the grating acts as a simple mirror and no wavelength dispersion is present. With SW in the SET position, the monochromator is driven through the region of the zero order in a selected direction of drive for backlash take-up. The position of the stepper motor which corresponds to the minimum value of D is noted. The stepper motor position is stored as a count in an electronic counter in $\mu$P and this counter can be set to zero at the minimum value of D. The number of steps needed to reach the region of the chosen line is predetermined and motor 20 is now driven through this number of steps. The motor is then driven slowly in the selected direction of drive through the line position in steps of typically 0.025 nm, and the digitised D value noted at each step. The step count corresponding to the minimum D value is stored. The motor is then reversed rapidly through the line and the peak search is repeated as a check on the step count. If the step counts agree, the motor is again reversed through the line and driven forward to the step count corresponding to the minimum D value. If they do not agree, which could happen if flame noise is present on the detector output, an error can be signalled to the operator. For this reason wavelength setting may be carried out via the reference path 31 with the moveable mirrors 9 and 10 intercepting the radiation and diverting it clear of the flame. If, however, wavelength setting is done via the sample path with a blank sample being atomised, the value of D obtained at the wavelength peak will be the value to be used in subsequent measurements.

In servo loops which are opened and closed there are unavoidable closure offset errors, which in the present case would shown up as an error in the value of D for optimum gain. The closure off-set error is repeatable however and its value can be determined and stored. It can then be subtracted from the stored value of D before this is supplied to DAC for gain setting in the RUN position of switch SW.

The use of the zero order as a reference point for wavelength setting is desirable since thermal expansion and contraction of the monochromator structure will produce the same shift in position of the zero order as it does to the first order spectral line.

If gain setting is carried out via the reference path, the DAC output may be corrected to compensate for the radiation loss which occurs at the four additional mirrors present in the reference path shown in FIG. 1. A comparison of the D signal obtained via the reference path with that obtained via the sample path can provide a correction factor for DAC output used when making measurements via the sample path.

In the foregoing description a sequence of events in time has to be controlled if the operation of the spectrophotometer is to be made largely automatic. These events include the movements of the moveable mirrors 9 and 10 to select either the sample or reference paths, the control of the automatic sampler AS and the atomiser control ATC, the monochromator slit control MSC and wavelength selection control MWC, the control of the switch SW and the selection of the times at which the ADC output will be stored and at which the DAC output will be provided. Also a store must be provided for the ADC outputs obtained on gain and wavelength setting. Calculations must also be made to select the stepper motor position for the peak wavelength from amongst the sets of values of D and motor position obtained as the monochromator is fine tuned. The loop closure error correction and the reference path correction calculations must also be made at the right times.

In FIG. 2 these events are timed and the calculations made by a microprocessor MCP. The microprocessor comprises a central processor $\mu P$, a read only memory ROM containing instructions and fixed data, and a random access memory, RAM for receiving input from and outputting data to a data bus BS. Using the microprocessor clock pulses as a time source, a time base can be generated. The ROM contains stored times for the events and can output instructions via the data bus BS to implement the events when their times are reached. The sets of values of stepper motor position and ADC values obtained during wavelength setting are stored in RAM and are operated upon by $\mu P$ in accordance with a stored programme in ROM to produce the stepper motor position for the resonance line peak. Likewise the loop closure error correction and the reference path calculations can be made by $\mu P$ in accordance with stored programmes and data held in ROM.

The invention has been described in relation to an atomic absorption spectrophotometer in which the sample is atomised in a flame. However the invention is equally applicable to an atomic emission spectrophotometer in which the radiation source is provided by the sample suitably exited to emit radiation of the selected spectral line wavelength. In this event, calibration is carried out using a sample having a maximum expected concentration of the element to be investigated so that the maximum detector signal is obtained at this maximum concentration.

What is claimed is:

1. A spectrophotometer comprising a source of radiation, a monochromator arranged to receive radiation from the source, a detector for receiving a selected wavelength of radiation from the monochromator and producing a signal representative of the intensity of the radiation received, means for comparing the output of the detector with a reference value when the spectrophotometer is in a calibration mode and producing a control signal dependent on the comparison, means for feeding the control signal to a control input of the detector for controlling the gain thereof so as to cause its output to tend towards the reference value, means for storing said control signal, and means for applying the stored control signal to the control input of the detector when the spectrophotometer is in a measurement mode characterised in that the spectrophotometer is an atomic spectrophotometer and includes a source of resonance line radiation, means for stepping the selected wavelength of the monochromator through the resonance line when the spectrophotometer is in the calibration mode, means for detecting the magnitude of the control signal when the gain of the detector is at a minimum value, means for detecting the wavelength setting of the monochromator when the gain of the detector is at a minimum value, means for storing the magnitude of the control signal and the wavelength setting which give the minimum detector gain, and means for applying the stored control signal to the detector and the stored wavelength setting to the monochromator when the spectrophototmeter is in the measurement mode.

2. An atomic spectrophotometer as claimed in claim 1, wherein the spectrophotometer is an atomic absorption spectrophotometer characterised in that radiation from the source is passed through and is partly absorbed by an atomised sample and in that the stored control signal and stored wavelength setting are those obtained when a blank sample is atomised.

3. An atomic spectrophotometer as claimed in claim 1, wherein the spectrophotometer is an atomic emission spectrophotometer characterised in that said stored control signal and stored wavelength setting are those obtained when a sample containing a maximum concentration of the element is atomised.

4. An atomic spectrophotometer as claimed in claim 2, characterised in that a sample path in which the sample is atomised is provided for the radiation between the source and the monochromator, in that an alternative reference path which excludes the sample is provided for the radiation between the source and the monochromator, and in that means are provided for deriving the stored wavelength setting and the stored control signal while the radiation is diverted via the reference path.

5. An atomic spectrophotometer as claimed in claim 4, characterised in that the radiation passes to the detector via the sample path during sample measurements and via the reference path between sample measurements in the calibration mode.

6. An atomic spectrophotometer as claimed in claim 5, characterised in that the sample measurements and the calibration are carried out automatically under the control of a microprocessor, the stored control signal and stored wavelength setting obtained in the calibration mode being digitized and stored in the microprocessor memory for use during sample measurements.

7. An atomic spectrophotometer as claimed in claim 6, characterised in that the reference value is a d.c. voltage and in that an amplified difference between this voltage and the detector signal comprises said control signal.

8. An atomic spectrophotometer as claimed in claim 7, characterised in that said detector comprises a photomultiplier tube, and in that said control input is connected to means for varying the dynode potentials of the electron multiplier section of the photomultiplier tube to vary the detector gain.

9. An atomic spectrophotometer as claimed in claim 4, characterized in that said detector comprises a photomultiplier tube, and in that said control input is connected to means for varying the dynode potentials of the electron multiplier section of the photomultiplier tube to vary the detector gain.

10. An atomic spectrophotometer as claimed in claim 3, characterized in that said detector comprises a photomultiplier tube, and in that said control input is connected to means for varying the dynode potentials of the electron multiplier section of the photomultiplier tube to vary the detector gain.

11. An atomic spectrophotometer as claimed in claim 2, characterized in that said detector comprises a photomultiplier tube, and in that said control input is connected to means for varying the dynode potentials of the electron multiplier section of the photomultiplier tube to vary the detector gain.

12. An atomic spectrophotometer as claimed in claim 1, characterized in that said detector comprises a photomultiplier tube, and in that said control input is connected to means for varying the dynode potentials of the electron multiplier section of the photomultiplier tube to vary the detector gain.

* * * * *